United States Patent [19]

Butler

[11] 4,236,082
[45] Nov. 25, 1980

[54] METHOD AND APPARATUS FOR RECORDING IMAGE DETAILS OF THE PALM OF A HAND

[75] Inventor: Marlow D. Butler, Portland, Oreg.

[73] Assignee: Palmguard, Inc., Beaverton, Oreg.

[21] Appl. No.: 7,345

[22] Filed: Jan. 29, 1979

[51] Int. Cl.³ .......................... G01N 21/38; G06K 9/00
[52] U.S. Cl. ................................. 250/461 R; 250/459; 340/146.3 E
[58] Field of Search ................... 250/461 R, 372, 271, 250/329, 458, 459; 340/146.3 E, 146.3 F; 354/62, 109; 356/71

[56] References Cited

U.S. PATENT DOCUMENTS

| | | | |
|---|---|---|---|
| 1,891,348 | 12/1932 | Ellinger et al. | 250/459 |
| 2,347,671 | 5/1944 | Dircksen | 250/461 R |
| 3,422,446 | 1/1969 | Riggles | 354/62 |
| 4,003,656 | 1/1977 | Leventhal | 340/146.3 E |
| 4,070,577 | 1/1978 | Lewis et al. | 250/461 R |
| 4,152,723 | 5/1979 | McMahon et al. | 250/458 |

Primary Examiner—Alfred E. Smith
Assistant Examiner—Carolyn E. Fields
Attorney, Agent, or Firm—George T. Noe

[57] ABSTRACT

A method and apparatus for enhancing image details of an object to be recorded. The object, such as the palm of a hand, is bombarded by radiant energy from an ultraviolet light source in such a manner that the object absorbs the radiant energy and emits visible light in the form of fluorescence and phosphorescence. A camera optically scans the object and records image details that have become available due to the fluorescence and phosphorescence. The details of objects having rough or irregular surfaces may be further enhanced by disposing the ultraviolet light source at an angle with respect to the surface of the object so that portions thereof are shaded while other portions of the surface absorb the radiant energy and emit visible light. Appropriate filters may be provided to reduce the effects of extraneous light.

10 Claims, 2 Drawing Figures

METHOD AND APPARATUS FOR RECORDING IMAGE DETAILS OF THE PALM OF A HAND

BACKGROUND OF THE INVENTION

In identification systems based on pattern recognition, it is important that prominent image details and features be repeatably provided to the identification system. One method of providing the prominence of such details is the process of electrical enhancement of the electrical analog signal output of a recording camera. The electrical analog signal corresponds to light levels obtained from an image as it is scanned by the camera. The enhancement provides a greater pronunciation of light and dark levels, and such enhancement may be achieved by a conventional differentiating network consisting of a series capacitor and a shunt resistor.

It would be desirable to enhance the image details before they are recorded by the camera so that the analog signal better represents prominent details, thereby reducing the number of light-to-dark and dark-to-light variations to which post-camera enhancement circuits must respond, and in turn increasing the reliability of subsequent image or pattern recognition. For example, the palm of the human hand includes both friction ridges and creases; however, the crease details are far more prominent than the friction ridge details. Thus it would be desirable to present to the camera only the crease details.

When illuminated or flashed by visible incoherent light, the palm of the human hand reflects the light in such a manner that a camera cannot detect subtle pattern changes caused by irregular surface details such as ridges and creases. For this reason, mere illumination of the palm by visible light does not provide the desired enhancement, and, in fact, may even obscure certain details.

It is well known that most objects, when illuminated by light of a given wavelength, will either reflect or absorb the light. In many materials, the light emanating from the object is of a different wavelength than that of the incident light, and this phenomenon is known as luminescence. One type of luminescence is fluorescence, a radiative form of energy which occurs in accordance with the theory of quantum mechanics wherein an atom which has been excited by an external energy source relaxes from one state to another, giving up a quantum of energy in the form of light. Another type of luminescence that is caused by the absorption of radiations and continues for a noticeable time after the radiations have stopped is phosphorescence. Generally, the term fluorescence is used to indicate that the emitted radiation continues only as long as the excitation continues, and the term phosphorescence is used to indicate that the emitted radiation continues for some time after the excitation has ceased. It is generally recognized that the dividing line between these two types of luminescence is a decay time of $10^{-8}$ second.

Both fluorescence and phosphorescence can result from excitation by an ultraviolet light source, and depending upon the length of time that radiations therefrom are applied to a substance can excite the substance to a level of energy which will produce luminescence from some period of time until the energy level decays to a level which no longer emits a desired level of visible light. Fluorescent decay technology is utilized in laboratory research to aid in determining the presence of certain molecules in complex organic samples. One example of the use of phosphorescence is in radar indicator devices wherein latent target images decay slowly to permit tracking of aircraft.

SUMMARY OF THE INVENTION

The present invention is related to identification systems in general, and in particular to a method and apparatus for enhancing the image details of an object before recording by a camera of an identification system.

To develop recognition data relating to a particular object or individual, an identification system includes a camera such as a vidicon or a solid-state charge-coupled image sensor which scans an identification object, which may be the palm of a human hand, and produces an electrical analog signal proportional to the light levels encountered as the ridges and valleys of the palm are scanned.

Prior to scanning by the camera, the palm is placed in position and flashed or strobed by an ultraviolet light source so that the palm absorbs radiant energy. During the ultraviolet excitation and after termination thereof, the palm emits visible light for a short period of time during which the aforementioned camera records image details that have become available due to fluorescence and phosphorescence. The variation of light levels emitted by the friction ridges under such luminescence is very slight, even though the variations are generally greater than can be obtained by illumination by a visible light source, while the variation of the light levels emitted by the creases under luminescence is substantial. It is believed that this is due at least in part to the differences in molecular density of the skin as well as differences in surface irregularities and textures. Therefore, the palm crease details are enhanced and thereby facilitate a positive identification.

It has been found that optimum enhancement is achieved by orienting the palm in such a manner that it is at an oblique angle to the ultraviolet light source and at the same time perpendicular to the camera. During ultraviolet flash, valley portions of the palm print details are shaded and remain dark, while the tops of the ridges and high surfaces absorb radiant energy. Those portions which absorb radiant energy are those which fluoresce and phosphoresce.

Appropriate filters may be provided to filter out extraneous light both during ultraviolet flash and during camera recording.

It is therefore one object of the present invention to provide a novel method and apparatus for recording image details for use in an identification system.

It is another object to provide enhancement of prominent image details of an object to be recorded by the utilization of the fluorescent and phosphorescent properties of the object.

It is a further object to provide an apparatus which repeatably provides prominent image details of an object to an identification system.

Further objects, features, and advantages will become apparent from consideration of the following description taken in conjunction with the accompanying drawings.

DRAWINGS

FIG. 1 is a block diagram of a preferred embodiment of the present invention; and FIG. 2 shows a cross section of an object receiving light energy from an oblique angle.

DETAILED DESCRIPTION OF THE DRAWINGS

Figure 1:
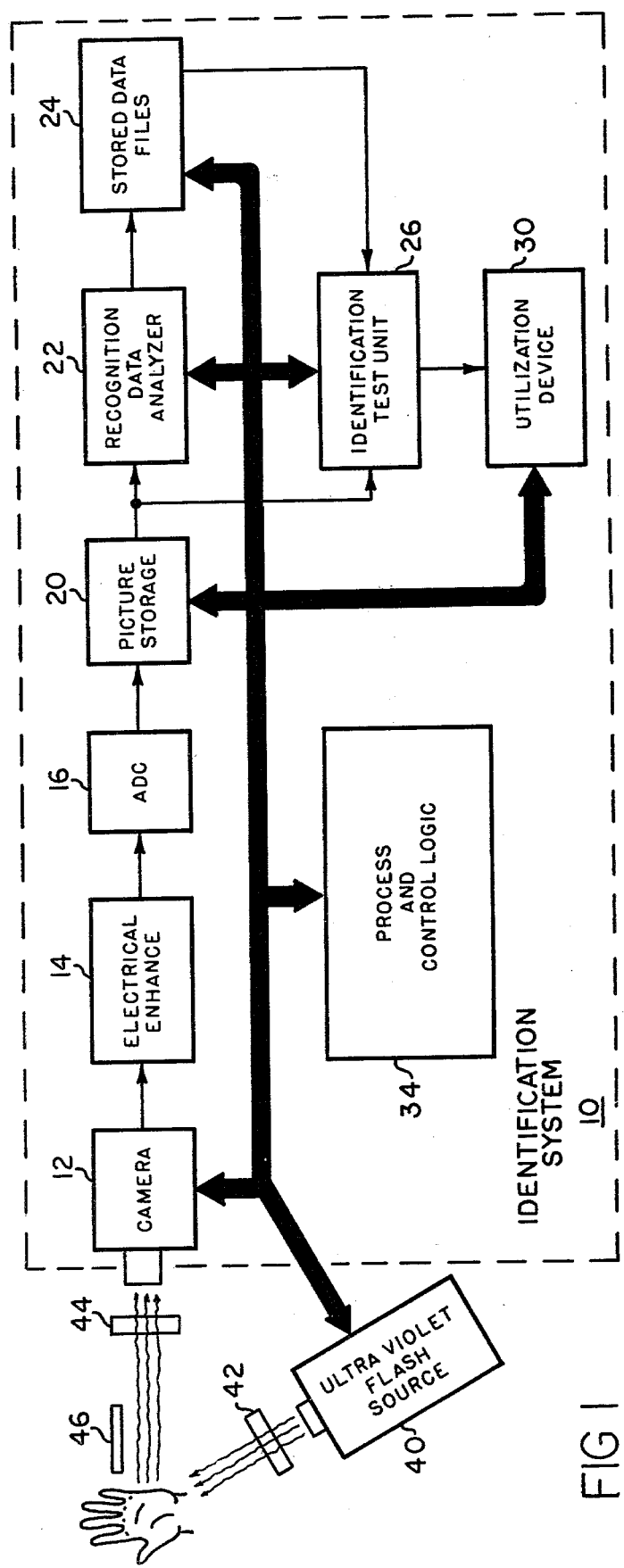

Turning now to FIG. 1, there is shown a block diagram of an identification system including pre-camera enhancement of image details, particularly those of the palm of the human hand. An identification system 10 includes a camera 12 for recording image details. The camera suitably may be a television-type vidicon or a solid-state charge-coupled image sensor, such as a Fairchild CCD 202 camera. This camera raster-scans an image, outputting an analog voltage signal which corresponds to the light levels obtained from the image on each horizontal scan. An enhance circuit 14, which may be a conventional differentiating circuit such as a series capacitor and a shunt resistor, may be provided to perform an electrical enhancement of the recorded image details, if such electrical enhancement is needed or desired. The analog signal, whether electrically enhanced or directly from the camera, is quantized by the analog-to-digital converter (ADC) 16 to provide numerical digital data which corresponds to the various voltage levels quantized. Many conventional analog-to-digital converters are available for this purpose.

The quantized or "digitized" signal is then stored in a picture storage unit 20 line by line as the image is scanned so that a complete digitized picture is stored therein. Such a storage unit may include 10,000 or more addressable storage elements.

A recognition data analyzer 22 is provided to perform an element-by-element analysis of the pattern image stored in the picture storage unit 20. The recognition data analyzer 22 includes a number of read-only memories (ROM's) containing specific logic steps for non-destructively analyzing each storage element under program control to pick out the prominent image details and rank them according to their prominence. The more prominent of the image details are then stored in stored data files 24, which data files suitably may be any storage medium intended for permanent storage, such as magnetic discs, tapes, cassettes, or cards. The data may be retrieved later upon command for identity verification.

The identity verification is performed by an identification test unit 26, which compares old picture information stored in data files 24 with newly-obtained picture information which has been loaded into the picture storage unit 20. The identification test unit 26 includes ROM's which contain specific logic steps to correlate the data under program control. In addition, the recognition data analyzer 22 may be called upon to pick out the prominent details as was done for the original data acquisition. A decision is made by the identification test unit 26 as to whether a reasonable match exists between the stored recognition data and the new recognition pattern, and an output signal is applied to a utilization device 30 indicating verification or rejection of the new recognition pattern. Thus, utilization device 30 suitably may include an electro-mechanical door-opening device, indicator lights, or an alarm.

A process and control logic unit 34 is provided to control the operation and operating sequence of the camera and circuits of the identification system 10. This process and control logic unit 34 suitably may be minicomputer or microprocessor hardware. Both have been successfully utilized in developing prototypes of the present invention, and the commercial embodiment employs a microprocessor. Identification system 10 suitably may be that described completely in patent application Ser. No. 817,623, filed July 21, 1977 now U.S. Pat. No. 4,186,378, and assigned to the assignee of the present invention.

Pre-camera enhancement is provided by utilization of the fluorescent and phosphorescent properties of the object to be recorded, which object in this instance is the palm of a human hand, as mentioned hereinabove. The hand is placed in position, perhaps by means of a suitable jig (not shown) to ensure repeatable readings, with the palm exposed to both an ultraviolet light source 40 and the camera 12. Preferably, the palm is oriented in such a manner that it is at an oblique angle to the ultraviolet light source 40 and at the same time perpendicular to camera 12 for reasons which will become apparent later. The identification system 10 may be actuated by any of a number of methods; for example, the person to be identified may enter an identity code into a keyboard, or he may insert a magnetized identification card into a card reader. Upon actuation of the identification system, the process and control logic unit 34 begins its predetermined identification sequence. First, the ultraviolet light source 40 is turned on, providing an ultraviolet flash or strobe of radiant energy, which is absorbed by the palm. During the ultraviolet excitation and after termination thereof, the palm emits visible light for a short period of time during which image details, primarily those of the crease lines, become available due to fluorescence and phosphorescence. The variation of light levels emitted by the friction ridges under such luminescence is very slight compared with the variation of light levels emitted by creases and adjacent areas. It should be mentioned that the creases themselves actually appear as dark lines against the brighter adjacent areas. It is believed that because the skin of the palm is stretched when the hand is open, the molecular density of the skin in the crease lines becomes lower than the density of other areas, and as a consequence of the quantum mechanics involved, the relatively fewer atoms absorb less radiant energy and give off less visible light. Therefore, the crease details appear to the camera to be dark lines.

The flash duration of the ultraviolet light source 40 is approximately one millisecond. Typically, the time required for the scanning and recording operation by camera 12 is about ten milliseconds.

Optical filters 42 and 44 may be provided whereby filter 42 passes light having a wavelength of from 350 to 400 nanometers to ensure that only ultraviolet light reaches the palm, and whereby filter 44 passes light having a wavelength of from 450 to 550 nanometers to ensure that only visible light reaches the camera 12.

A mirror 46 may be provided to ensure complete and even coverage of the palm by bouncing what would otherwise be extraneous ultraviolet light back onto the palm during the flash period. Even under such bounce light operation, however, the valley portions and other low portions of the palm, including the crease details, are shaded.

When the palm detail information has been recorded by camera 12, the identification system operates on the stored information under control of the process and control logic unit 34 as described hereinabove, and the hand may be removed from the predetermined palm position.

Figure 2:
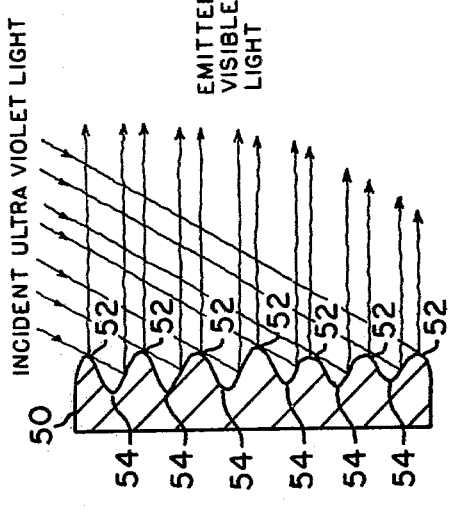

It can be appreciated with reference to FIG. 2 that when light strikes an object 50 having peaks 52 and valleys 54 from an oblique angle, the valleys 54 do not receive the incident light and are thus shaded. Therefore, light is reflected substantially from just the peaks 52. It is for this reason that it is preferable to orient the palm so that ultraviolet light from flash source 40 strikes the surface of the palm at an oblique angle. This ensures that the crease details will absorb less radiant energy and that the image details of the palm will be enhanced.

While I have shown and described a preferred embodiment of the present invention, it will be obvious to those skilled in the art that many changes may be made without departing from the invention in its broader aspects.

What I claim as being novel is:

1. In an identification system, a method of recording image details of the palm of a hand, comprising the steps of:
    bombarding the palm with radiant energy so that said palm absorbs the radiant energy and emits visible light from the surface thereof, the levels of visible light varying in accordance with the characteristics of the palm and the surface thereof;
    optically raster-scanning the surface of said palm to sense the varying levels of light and to develop an analog electrical signal proportional thereto; and
    processing said analog signal to record a complete picture of said image details.

2. A method in accordance with claim 1 wherein said radiant energy is in the form of ultraviolet light and said visible light is in the form of fluorescence and phosphorescence.

3. A method in accordance with claim 1 wherein said radiant energy is directed toward said palm from an angle.

4. A method in accordance with claim 1 wherein said step of bombarding the palm with radiant energy has a time duration of about one millisecond.

5. In an identification system, an apparatus for recording image details of the palm of a hand, comprising:
    means for bombarding the palm with radiant energy so that said palm absorbs the radiant energy and emits visible light from the surface thereof, the levels of visible light varying in accordance with the characteristics of the palm and the surface thereof;
    means for optically raster-scanning the surface of said palm to sense the varying levels of light and develop an analog electrical signal proportional thereto; and
    means for processing said analog signals to record a complete picture of said image details.

6. An apparatus in accordance with claim 5 wherein said bombarding means comprises an ultraviolet light source, said radiant energy being in the form of ultraviolet light and said emitted visible light being in the form of fluorescence and phosphorescence.

7. An apparatus in accordance with claim 6 further including a first optical filter disposed between said ultraviolet light source and said palm; and a second optical filter disposed between said said palm and said optical raster-scanning means, said first optical filter passing light having a wavelength of from about 350 to 400 nanometers, and said second optical filter passing light having a wavelength of from about 450 to 550 nanometers.

8. An apparatus in accordance with claim 6 further including a mirror disposed adjacent to said palm, said mirror being oriented to reflect said ultraviolet light onto said palm.

9. An apparatus in accordance with claim 6 wherein said ultraviolet light source is disposed at an angle with respect to the surface of said palm so that certain portions of said palm are shaded from said radiant energy.

10. An apparatus in accordance with claim 6 further including control means connected to said ultraviolet light source and said optical raster-scanning and said processing means for controlling the operation and operating sequence thereof.

* * * * *